United States Patent [19]
Chiknas

[11] Patent Number: 4,470,954
[45] Date of Patent: Sep. 11, 1984

[54] ROTOR OR CARRIER FOR CENTRIFUGAL ANALYZER AND BEAD WASHER

[76] Inventor: Steven G. Chiknas, 111 Wolf Trap Rd., Vienna, Va. 22180

[21] Appl. No.: 503,603

[22] Filed: Jun. 13, 1983

[51] Int. Cl.³ ..................... G01N 21/07; G01N 33/50
[52] U.S. Cl. ..................... 422/72; 422/64; 422/104; 436/45
[58] Field of Search ............ 422/72, 73, 102, 104, 422/64; 436/45, 809; 494/27, 42, 85

[56] References Cited

U.S. PATENT DOCUMENTS

| | | | |
|---|---|---|---|
| 3,464,798 | 9/1969 | Kilthau | 422/102 |
| 3,555,284 | 1/1971 | Anderson | 436/45 |
| 3,582,218 | 6/1971 | Anderson | 356/427 |
| 3,681,029 | 8/1972 | Shapiro | 422/104 |
| 3,684,450 | 8/1972 | Alder et al. | 436/45 |
| 3,759,666 | 9/1973 | Hill, Jr. | 435/14 |
| 3,826,619 | 7/1974 | Bratu, Jr. | 422/71 |
| 3,856,470 | 12/1974 | Cullis et al. | 422/64 |
| 3,902,660 | 9/1975 | Barber | 494/11 |
| 4,020,151 | 4/1977 | Bolz et al. | 436/527 |
| 4,067,959 | 1/1978 | Bolz | 436/518 |
| 4,092,114 | 5/1978 | Buck | 436/513 |
| 4,123,173 | 10/1978 | Bullock et al. | 356/246 |
| 4,133,639 | 1/1979 | Harte | 436/518 |
| 4,147,752 | 4/1979 | Suovaniemi et al. | 422/57 |
| 4,197,287 | 4/1980 | Piasio et al. | 436/518 |
| 4,210,622 | 7/1980 | Soothill et al. | 422/61 |
| 4,226,531 | 10/1980 | Tiffany et al. | 356/246 |
| 4,314,968 | 2/1982 | Guigan | 422/72 |

*Primary Examiner*—Michael S. Marcus
*Assistant Examiner*—Joseph P. Carrier
*Attorney, Agent, or Firm*—Kerkam, Stowell, Kondracki & Clarke

[57] ABSTRACT

A bead holder comprising a disc-like member having a central opening and having on its top surface a plurality of wells each adapted to receive a spherical bead is disclosed. The wells are defined by an outer peripheral wall, an inner wall, a bottom wall and a pair of side walls. Each outer peripheral wall is provided with an aperture therethrough which communicates with an upper part of the well whereby liquid is maintainable in the wells and removable from the wells by centrifugal force. The bead holder is preferably sized to be releasably mounted on the rotor of a centrifugal analyzer or on a centrifugal bead washer which also forms a part of the present invention.

5 Claims, 6 Drawing Figures

ROTOR OR CARRIER FOR CENTRIFUGAL ANALYZER AND BEAD WASHER

TECHNICAL FIELD

The present invention concerns a novel centrifugal system for removing excess and unbound reagents during the performance of coated sphere immunoassays.

BACKGROUND OF THE PRIOR ART

It is well known in the art to provide centrifugal analyzers and systems for performance of homogeneous immunoassays and examples of such devices and systems are found in the following U.S. patents:
U.S. Pat. No. 3,555,284, Anderson
U.S. Pat. No. 3,582,218, Anderson
U.S. Pat. No. 3,681,029, Shapiro
U.S. Pat. No. 3,759,666, Hill, Jr.
U.S. Pat. No. 3,856,470, Cullis et al.
U.S. Pat. No. 3,902,660, Barber
U.S. Pat. No. 4,123,173, Bullock et al.
U.S. Pat. No. 4,266,531, Tiffany et al.

THE PRESENT INVENTION

It is an object of the present invention to provide a system for the performance of heterogeneous immunoassays and for separation of an antigen or antibody attached to a sphere.

Another objective of the present invention is to provide a rotatable carrier for such spheres containing a plurality of reaction wells into which such spheres are placed for the duration of the assay.

A futher object of the present invention is to provide a channel and barrier system in such reaction wells such that appropriate amounts of reactant liquid may be added and retained for set periods of reaction time. Following such reaction time the carrier can be rotated at a sufficient speed to force all liquid in the reaction well against the outer wall. Due to the unique construction of the reaction well, the spheres are retained in the reaction wells by the incorporated barriers while the reactant liquid is channeled off to an appropriate waste receptacle.

A still further object of the present invention is to provide rotatable carriers which will, due to their size, shape and capacity, be compatable with centrifugal analyzers such that placement of a carrier with a completed reaction solution into a centrifugal analyzer will allow simultaneous reading of all standards and test solutions with subsequent automatic calculation of results by the analyzer.

In accordance with the present invention, a centrifuge is provided which includes a rotor having a rotatable shaft and an outer container capable of collecting and storing liquid removed from rotor wells by centrifugal force.

A circular bead holder is provided defining a central aperture and is adapted for positioning within the central opening of a centrifuge, with the rotatable shaft extending through the central aperture of the bead holder.

The bead holder defines on its top surface a plurality of wells for receiving spherical beads and constituents to be centrifuged. The bead holder has a peripheral wall facing the outer collection container of the centrifuge. The peripheral wall defines apertures which serve to direct the flow of liquid outward and downward from the bead holder wells to the outer container of the centrifuge.

In the illustrative embodiment, the bead holder wells comprise generally rectangular depressions defined by walls which taper radially outward. Each well contains two barrier pieces comprised of parallel vertical walls which define a central groove which tapers radially outward and serves during centrifugation to channel liquid from the bottom of the well to the aperture communicating with the outer container of the centrifuge. The bead holder may be formed as an integrally-molded plastic member.

BRIEF DESCRIPTION OF THE SEVERAL VIEWS OF THE DRAWING

A more detailed explanation of the invention is provided in the following description and claim, and is illustrated in the accompanying drawings wherein:

DETAILED DESCRIPTION OF THE INVENTION

Figure 1:
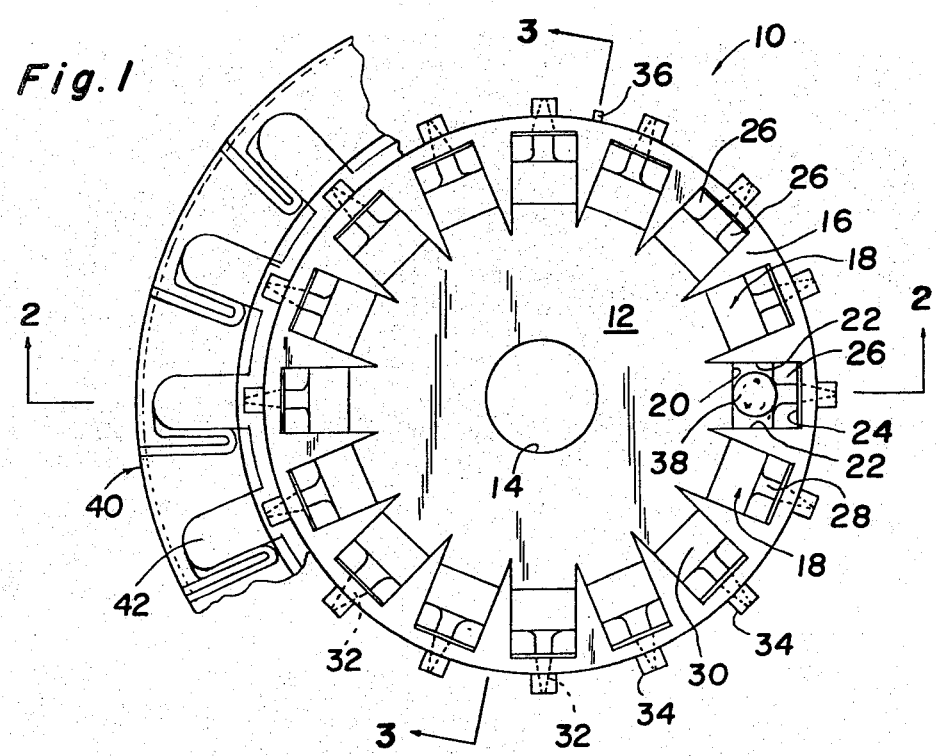
FIG. 1 is a fragmentary top plan view of a rotor and collector ring constructed in accordance with the teachings of the present invention.

Referring to FIGS. 1 through 4, 10 generally designates a circular bead holder which is preferably a unit molded from plastic, such as polystyrene, polypropylene or acrylic. Bead holder 10 is generally circular (disc-shaped) having a central hub portion 12 provided with a central opening 14.

Bead holder 10 has a main body portion 16 which defines a plurality of wells 18, each of which wells is bounded by an inner wall 20, a pair of side walls 22, and an outer wall 24. The outer wall 24 contains several features pertinent to the novelty of the invention. The outer wall is curved upwardly and outwardly to assist in liquid removals and two bead immobilization barriers 26 are incorporated into the outer wall 24 which define a groove 28 therebetween. The groove 28 serves to channel liquid during the centrifugation process from the bottom of a well 30 into the aperture 32 in the outer wall 24 of the bead holder.

The wells are generally rectangular and although no limitation is intended, the bead holder may contain fifty such wells, forty nine of which are utilized for actual analysis while one well is utilized for calibration purposes.

Along the outer periphery of bead holder 10 there are radially extending ribs 34, centrally positioned with respect to each well and carrying the apertures 32 through the peripheral wall of the bead holder, whereby the wells 18 each communicate through apertures 32 to the outside of the bead holder. There also exists along the outer periphery of bead holder 10 a solid positioning rib 36 which may serve as a point of reference for assigning a position number to each well.

Figure 2:
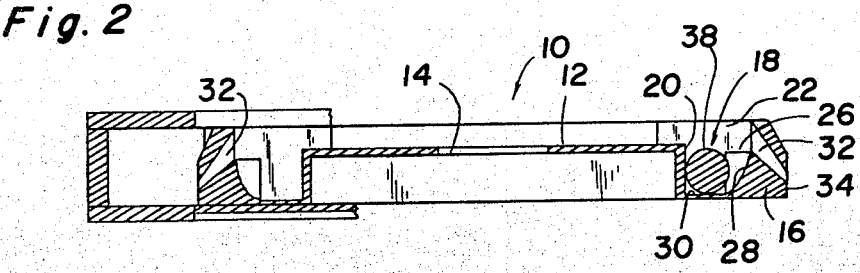
FIG. 2 is a section on line 2—2 of FIG. 1.
Figure 3:
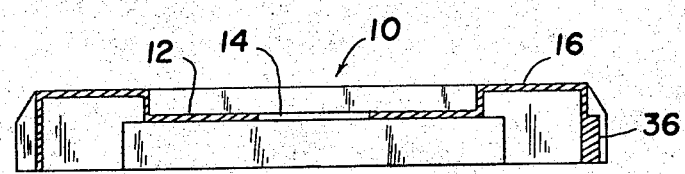
FIG. 3 is a section on line 3—3 of FIG. 1.
Figure 4:
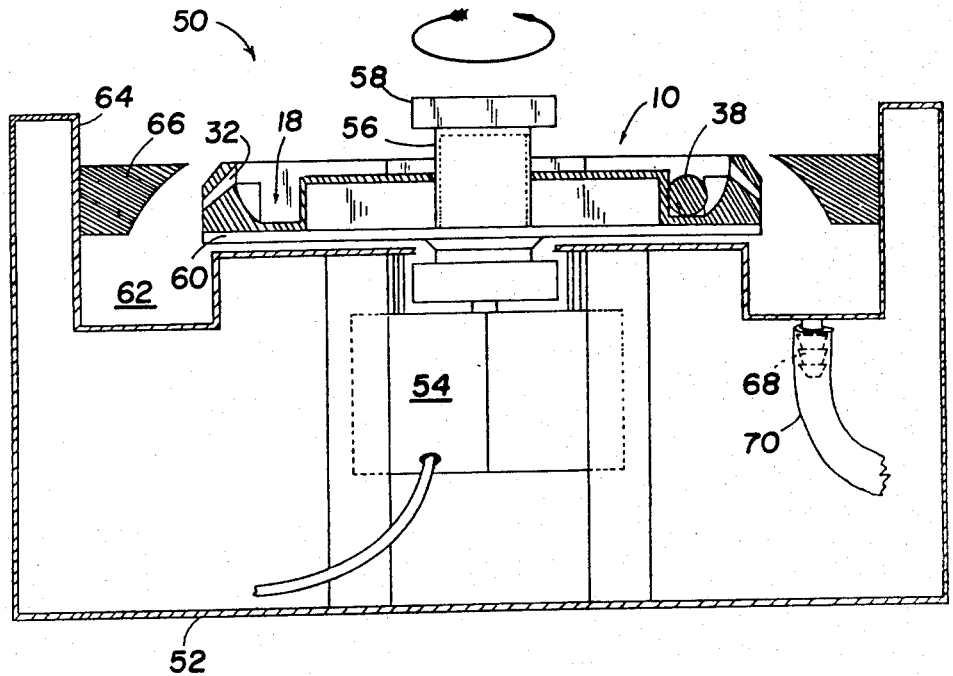
FIG. 4 is a fragmentary vertical sectional view of the rotor illustrated in FIG. 1 in conjunction with drive means and collection means for washing the spherical beads retained in the wells formed in the rotor.

The rotor bead holder is employed in conjunction with spherical beads 38, FIGS. 1, 2 and 4, which spherical beads are sized to be fitted in the space between wall 20 and the pair of bead immobilization barriers 26. The beads may also be formed of plastic or metal and cast or shaped in a conventional manner. The beads should be sized from about ⅛ to ½ inch and preferred size would be ¼ inch.

As illustrated in FIGS. 1 and 2, the ring or rotor 10 may be employed in conjunction with a collector ring as exists in the optical head of a centrifugal analyzer generally designated 40 which collector ring is provided with a plurality of liquid receiving chambers 42 which communicate with the wells 18 via the passages 32. Thus the chambers 42 provide means for collecting and reading the optical density or flourescence of the liquid or fluids from wells 18 when the structures 10 and 40 are centrifuged as is well known in the art.

Referring now to FIG. 4, the rotor or bead holder 10 may also be used in conjunction with an improved bead washer generally designated 50. The bead washer 50 comprises a container or housing 52, an electric motor 54, a spindle 56 having a retainer cap 58 associated therewith.

The rotor 10 is supported from its undersurface by a circular plate 60 which rotates with the spindle of the device. The housing 52 includes an annular trough 62 which is provided along an upper wall 64 with a shield 66 which shield ensures that wash liquid directed onto the rotor 10 and which wash liquid issues from the openings 32 of each well 18 enters the annular trough 62, to be drained therefrom via outlet 68 and, for example, tubing 70 as the bead holder or disc 10 is rotated.

Figure 5:
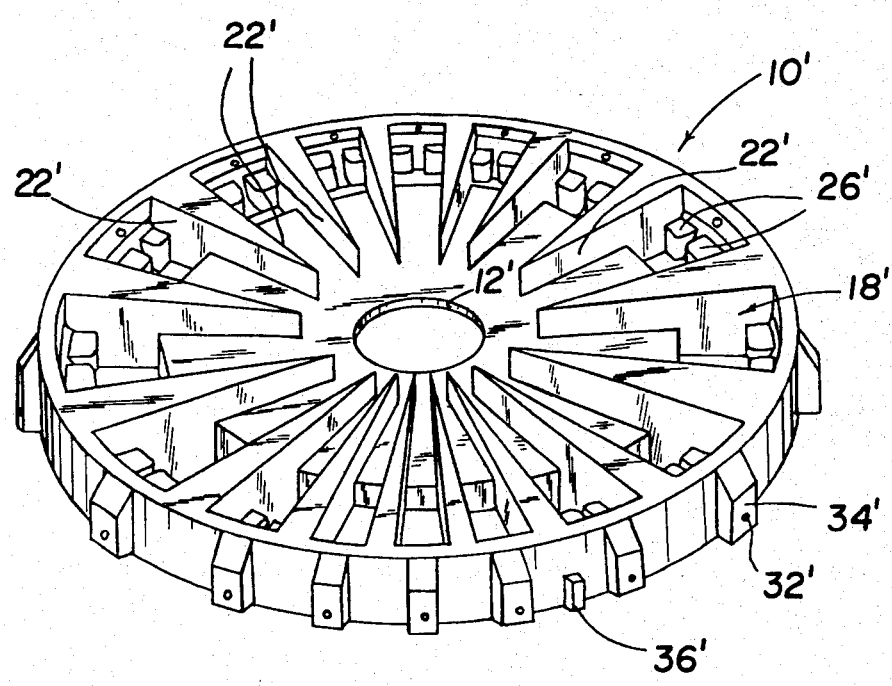
FIG. 5 is a perspective view of a modified form of the rotors of the invention.

Referring now to FIG. 5 of the drawing, a modified form of bead holder is illustrated and reference characters applied thereto denoting structures found in the rotor 10 are provided.

The bead holder or disc 10' is provided with a plurality of wells 18' which wells have bead barriers 26', fluid outlets 32' which communicate with an upper portion of each of the wells 18'. The outlets 32' are formed in radially extending ribs 34' and the device may include an indexing rib 36'. This form of the bead holder is only distinguishable in that the wells 18' have extended radial side walls 22' which terminate short of the hub 12'. The extended side walls 22' form barriers between the plurality of wells.

Figure 6:
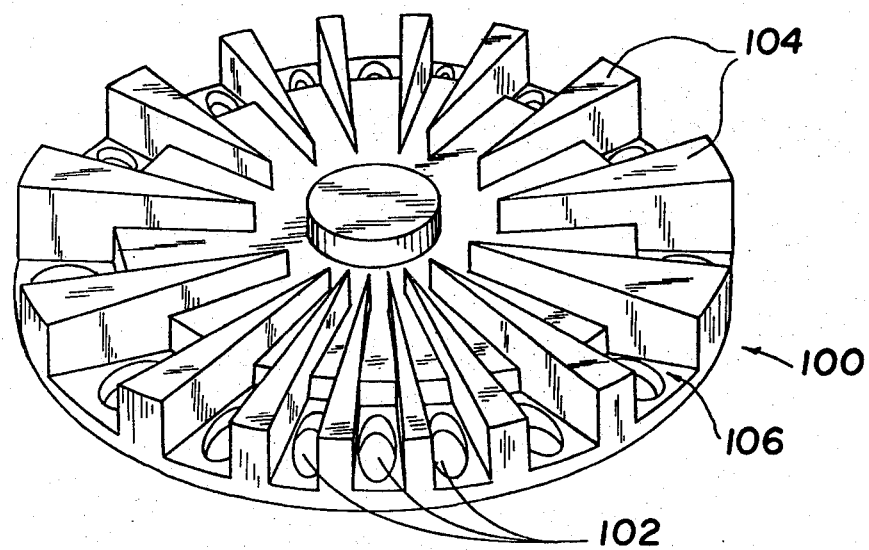
FIG. 6 is a perspective view of a base plate array for use with the bead holding rotor illustrated in FIG. 5.

Referring now to FIG. 6, there is illustrated a novel base plate 100 which is provided with a plurality of openings or ports 102 and upstanding webs or ribs 104 which ribs are sized to fit into and mate with the extended side walls 22' of the form of the bead holder 10' illustrated in FIG. 5 with each of the wells 18' fitting into the spaces generally designated 106 of the form-fitting base plate 100. The base plate 100 may be constructed of a lead alloy or other appropriate gamma- or X-ray or the like barrier as to be more fully discussed hereinafter.

In the operation of the system using nonradioisotopic immunochemical techniques, in a specific example spheres 38, precoated with an antibody directed against a specific analyte of interest, are loaded into wells 18-18' of bead holder 10-10'. An aliquot of serum or plasma to be assayed for the analyte of interest is introduced into the well. A solution containing an enzyme coupled to an antibody directed against the analyte of interest is also added to the well. The bead holder containing the spheres immersed in the sample-antibody-enzyme solution is then placed into an incubator and incubated at an appropriate temperature (for example 30° C.) for a time period sufficient to allow the immunologic reaction to proceed to equilibrium (for example, 30 minutes to 5 hours). Following the incubation period, the bead holder is placed in a centrifuge 50 and rotated such that all liquid is centrifuged out of the wells and into a waste receptacle 62, leaving the coated spheres in the wells.

Following centrifugation, wash buffer is added to each of the wells containing a sphere to redilute excess sample and enzyme reagent which has not bound to the spheres. The bead holder is then centrifuged to remove the wash solution. The wash procedure may be repeated a many times as deemed sufficient to remove all non-bound reactants.

When the spheres are free of all excess reagents, enzyme substrate solution (from 200 to 500 microliters) is then added to each well containing a sphere. The bead holder in then incubated at an appropriate temperature for an appropriate time to allow sufficient conversion of substrate to product by the enzyme attached to the sphere to allow a photomeric determination of the quantity of product produced. The reaction may then be stopped by the addition of an acid solution, which may also serve as a color developer. The presence of reaction product (as shown by the presence of a known coloring of the substrate solution) may now be determined qualitatively by inspection or quantitatively by sequentially drawing the solution from each well into the flow cell of a spectrophotometer or spectrofluorometer.

Alternatively, the bead holder may be constructed so as to be compatable with the cuvette array of a centrifugal analyzer, such as shown and described in U.S. Pat. No. 3,555,284 Anderson, whereupon at completion of the color development phase the bead holder may be placed into the centrifugal analyzer and the reaction solution centrifuged out into the centrifugal analyzer cuvettes where the absorbance of all of the reaction solutions may be quantitated simultaneously.

Following quantitation of the reaction solution, the excess reaction solution may be centrifuged out of the bead holder (this step is not necessary in centrifugal analyzer due to the internal wash cycle of the analyzer which will remove all excess solution automatically), and the spheres discarded by inverting the bead holder over a waste receptacle. The bead holder may now be washed and reused, or discarded.

In a specific example of a radioimmunoassay technique, spheres precoated with an antibody directed against an analyte of interest are placed into the wells. A serum or plasma sample is then placed into each well containing a sphere, along with a solution containing an antibody directed against the analyte of interest prelabeled with a gamma ray emitting radioisotope. The bead holder is then placed at an appropriate temperature for an appropriate period of time for immunologic association to occur. The bead holder is then placed into a centrifuge and all liguid is removed from the wells by centrifugation. The spheres are retained in the bead holder during this process. Wash solution is then added to each well containing a sphere, and the bead holder is again centrifuged to remove all wash liquid. The wash procedure is repeated a sufficient number of times to assure removal of all unbound radioisotopes.

The bead holder is then placed onto the form-fitting base plate 100 FIG. 6., which contains the circular openings 101 placed under each well. The base plate as described may be constructed of a lead alloy or some other appropriate material which serves as a gamma ray barrier. The base plate may now be placed into a gamma counter such that only one well at a time may be situated over the detector. The wells are then placed sequentially over the detector and the gamma ray emission of each sphere is quantitated. Following quantitation the spheres are discarded into a solid radioactive waste container and the bead holder may either be washed for reuse or discarded.

Although illustrative embodiments of the invention have been shown and described, it is to be understood that various modifications and subsititutions may be made by those skilled in the art without departing from the novel spirit and scope of the present invention.

I claim:

1. A bead holder comprising a disc-like member having a central opening and having on its top surface a plurality of wells, each said well being defined by an outer peripheral wall, an inner wall, a bottom wall and a pair of side walls, each said well having a pair of spaced barriers collectively attached to the peripheral wall, bottom wall and two side walls and defining a channel therebetween, each said well also having an outlet aperture through its peripheral wall which communicates with an upper part of the well whereby liquid is maintainable in the wells and removable from the wells by centrifugal force, each spaced barrier projecting radially inward from the peripheral wall and projecting out from one side wall and towards another side wall, said channel having communication at one end with the bottom wall of said well and at the other end with said outlet aperture; a spherical bead for each well, each of said spherical beads sized to be received in said wells and retained therein by said spaced barriers during rotation of the bead holder, and wherein each well is completely open-topped between its inner wall, side walls, and peripheral wall.

2. The bead holder defined in claim 1 wherein the outlet aperture slopes downwardly and outwardly.

3. The device defined in claim 1 in combination with a gamma-ray impervious disc, said ray impervious disc having a plurality of openings therein corresponding in position and number to the position and number of wells.

4. The device defined in claim 1 in combination with a bead washer, said bead washer comprising a hollow container, a top for the container, said top adapted to receive said bead holder and having an annular trough, a motor in the container having a vertical spindle projecting through the top and adapted to engage said bead holder with the outlet aperture from the wells positioned above the annular trough, and an outlet drain from said trough.

5. The invention defined in claim 4 wherein the annular trough is provided with an annular splash shield.

* * * * *